(12) United States Patent
Engman et al.

(10) Patent No.: US 10,957,453 B2
(45) Date of Patent: Mar. 23, 2021

(54) WCD SYSTEM ALERT ISSUANCE AND RESOLUTION

(71) Applicant: West Affum Holdings Corp., Grand Cayman (KY)

(72) Inventors: Zoie R. Engman, Kirkland, WA (US); David P. Finch, Bothell, WA (US); Joseph L. Sullivan, Kirkland, WA (US); Erick M. Roane, Bellevue, WA (US); Pamela F. Breske, Newcastle, WA (US)

(73) Assignee: West Affum Holdings Corp., Grand Cayman (KY)

( * ) Notice: Subject to any disclaimer, the term of this patent is extended or adjusted under 35 U.S.C. 154(b) by 0 days.

(21) Appl. No.: 16/542,110

(22) Filed: Aug. 15, 2019

(65) Prior Publication Data
US 2021/0050111 A1 Feb. 18, 2021

(51) Int. Cl.
*A61B 5/00* (2006.01)
*G16H 50/30* (2018.01)
(Continued)

(52) U.S. Cl.
CPC ......... *G16H 50/30* (2018.01); *A61N 1/37258* (2013.01); *A61N 1/3943* (2013.01); *A61N 1/3968* (2013.01); *A61N 1/3987* (2013.01)

(58) Field of Classification Search
CPC .... G16H 50/30; A61N 1/3968; A61N 1/3987; A61N 1/37258; A61N 1/3943;
(Continued)

(56) References Cited

U.S. PATENT DOCUMENTS 3,724,355 A 4/1973 Unger
4,583,524 A 4/1986 Hutchins
(Continued)

FOREIGN PATENT DOCUMENTS

EP 3434326 A1 1/2019
WO 1998039061 A2 9/1998
WO 2012064604 A1 5/2012

OTHER PUBLICATIONS

Extended European Search Report, based on Application No. 19206064.8, dated May 19, 2020, 8 pages.
(Continued)

*Primary Examiner* — An T Nguyen
(74) *Attorney, Agent, or Firm* — Christenson O'Connor Johnson Kindness PLLC

(57) ABSTRACT

In one embodiment, a WCD is described. The WCD includes a support structure configured to be worn by a patient and a processor coupled to the support structure. The WCD also includes an energy storage module configured to store an electrical charge and in communication with the processor. The WCD also includes a discharge circuit coupled to the energy storage module, the discharge circuit in communication with the processor and configured to discharge the stored electrical charge through a body of the patient. The processor is configured to detect an event at the WCD, classify the detected event, and determine an alarm onset time of the detected event based at least in part on the event classification. The processor is further configured to issue the alarm after the alarm onset time.

20 Claims, 5 Drawing Sheets

(51) Int. Cl.
  *A61N 1/39* (2006.01)
  *A61N 1/372* (2006.01)
(58) Field of Classification Search
  CPC .. A61N 1/3904; A61N 1/39931; A61B 5/746; A61B 5/0031; A61B 5/686; A61B 5/04012
  See application file for complete search history.

(56) References Cited

U.S. PATENT DOCUMENTS

| | | | |
|---|---|---|---|
| 4,619,265 A | 10/1986 | Morgan et al. | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,353,793 A | 10/1994 | Bornn | |
| RE34,800 E | 11/1994 | Hutchins | |
| 5,394,892 A | 3/1995 | Kenny | |
| 5,405,362 A | 4/1995 | Kramer et al. | |
| 5,474,574 A | 12/1995 | Payne et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lysler | |
| 5,913,685 A | 6/1999 | Hutchins | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder | |
| 6,437,083 B1 | 7/2002 | Owen et al. | |
| 6,529,875 B1 | 3/2003 | Nakajima | |
| 6,546,285 B1 | 4/2003 | Owen et al. | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,140,154 B2 | 10/2012 | Donnelly et al. | |
| 8,369,944 B2 | 2/2013 | Macho et al. | |
| 8,644,925 B2 | 2/2014 | Volpe et al. | |
| 8,676,313 B2 | 3/2014 | Volpe et al. | |
| 8,965,500 B2 | 2/2015 | Macho et al. | |
| 9,008,801 B2 | 4/2015 | Kaib et al. | |
| 9,131,901 B2 | 9/2015 | Volpe et al. | |
| 9,132,267 B2 | 9/2015 | Kaib | |
| 9,345,898 B2 | 5/2016 | Piha et al. | |
| 9,901,741 B2 | 2/2018 | Chapman et al. | |
| 10,016,613 B2 | 7/2018 | Kavounas | |
| 2002/181680 A1 | 12/2002 | Linder et al. | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2006/0173499 A1 | 8/2006 | Hampton et al. | |
| 2008/0312709 A1 | 12/2008 | Volpe et al. | |
| 2009/0005827 A1 | 1/2009 | Weintraub et al. | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0191476 A1 | 7/2012 | Reid et al. | |
| 2012/0265265 A1 | 10/2012 | Razavi et al. | |
| 2012/0283794 A1 | 11/2012 | Kaib et al. | |
| 2012/0293323 A1* | 11/2012 | Kaib | G08B 21/18 340/539.12 |
| 2012/0302860 A1 | 11/2012 | Volpe et al. | |
| 2013/0085538 A1 | 4/2013 | Volpe et al. | |
| 2013/0144355 A1 | 6/2013 | Macho et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0046391 A1 | 2/2014 | Cowan et al. | |
| 2014/0070957 A1 | 3/2014 | Longinotti-Buritonil et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0224330 A1* | 8/2015 | Kaib | A61N 1/3904 607/7 |
| 2015/0297904 A1 | 10/2015 | Kavounas | |
| 2016/0004831 A1 | 1/2016 | Carlson et al. | |
| 2016/0283900 A1 | 9/2016 | Johnson et al. | |
| 2016/0328529 A1* | 11/2016 | Kaib | G16H 40/40 |
| 2017/0278370 A1* | 9/2017 | Kaib | A61B 5/746 |
| 2017/0281099 A1* | 10/2017 | Averina | A61B 5/746 |
| 2017/0319862 A1 | 11/2017 | Foshee, Jr. et al. | |
| 2017/0367591 A1 | 12/2017 | Jorgenson | |
| 2018/0116537 A1* | 5/2018 | Sullivan | A61B 5/6802 |
| 2018/0184933 A1 | 7/2018 | Sullivan et al. | |
| 2018/0185662 A1 | 7/2018 | Foshee, Jr. et al. | |
| 2018/0243578 A1 | 8/2018 | Volosin | |
| 2019/0030352 A1 | 1/2019 | Sullivan et al. | |
| 2019/0076666 A1 | 3/2019 | Medema | |
| 2019/0282178 A1* | 9/2019 | Volosin | G16H 40/67 |
| 2019/0329054 A1* | 10/2019 | Breske | A61N 1/3993 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Jounal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

Heartstart MRx and XL AED Algorithm—Application Note, Jul. 2001, Edition 2 Phillips Healthcare, USA.

Zoll LifeVest Model 4000 Patient Manual PN 20B0047 Rev B, (C) 2009-2012.

* cited by examiner

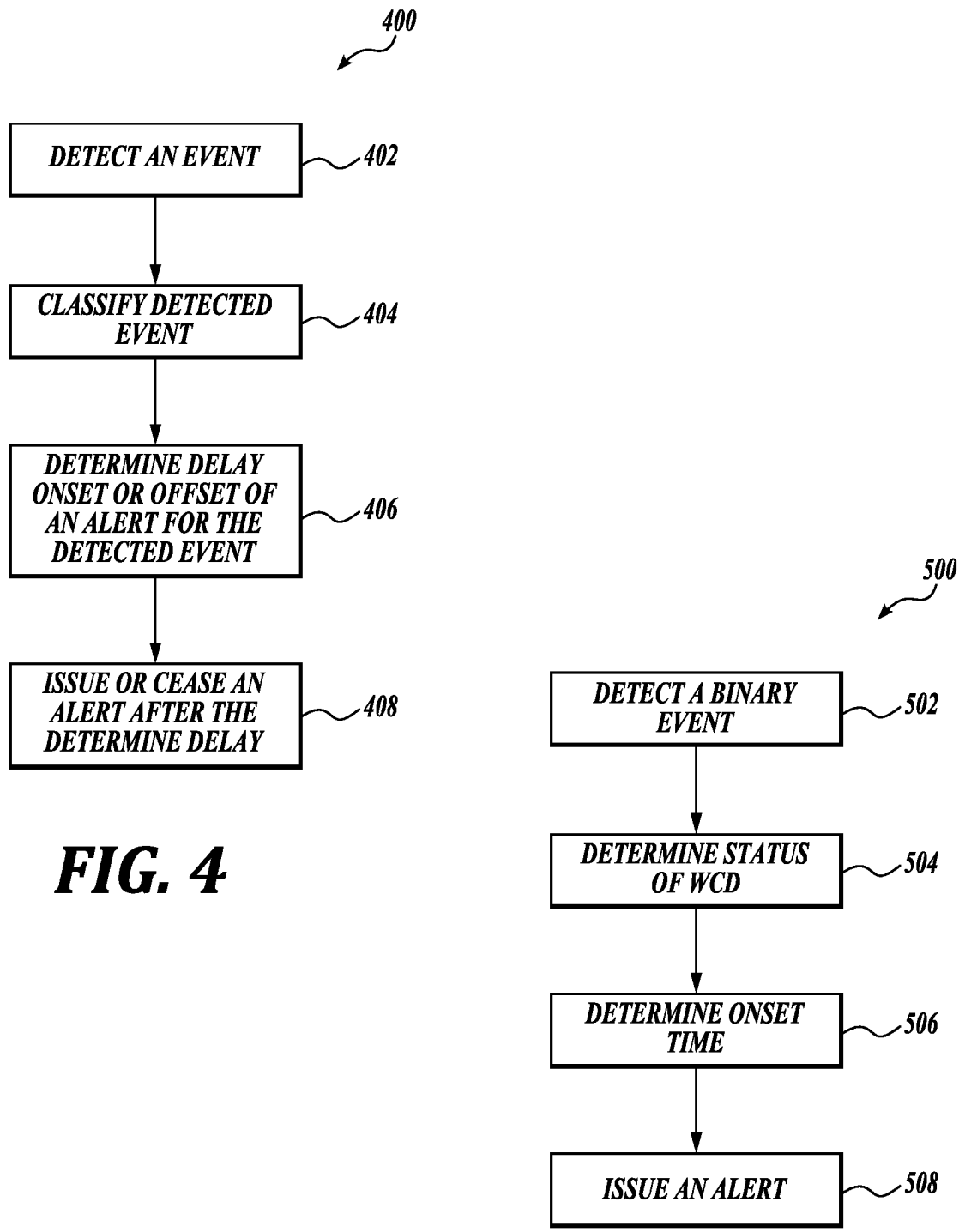

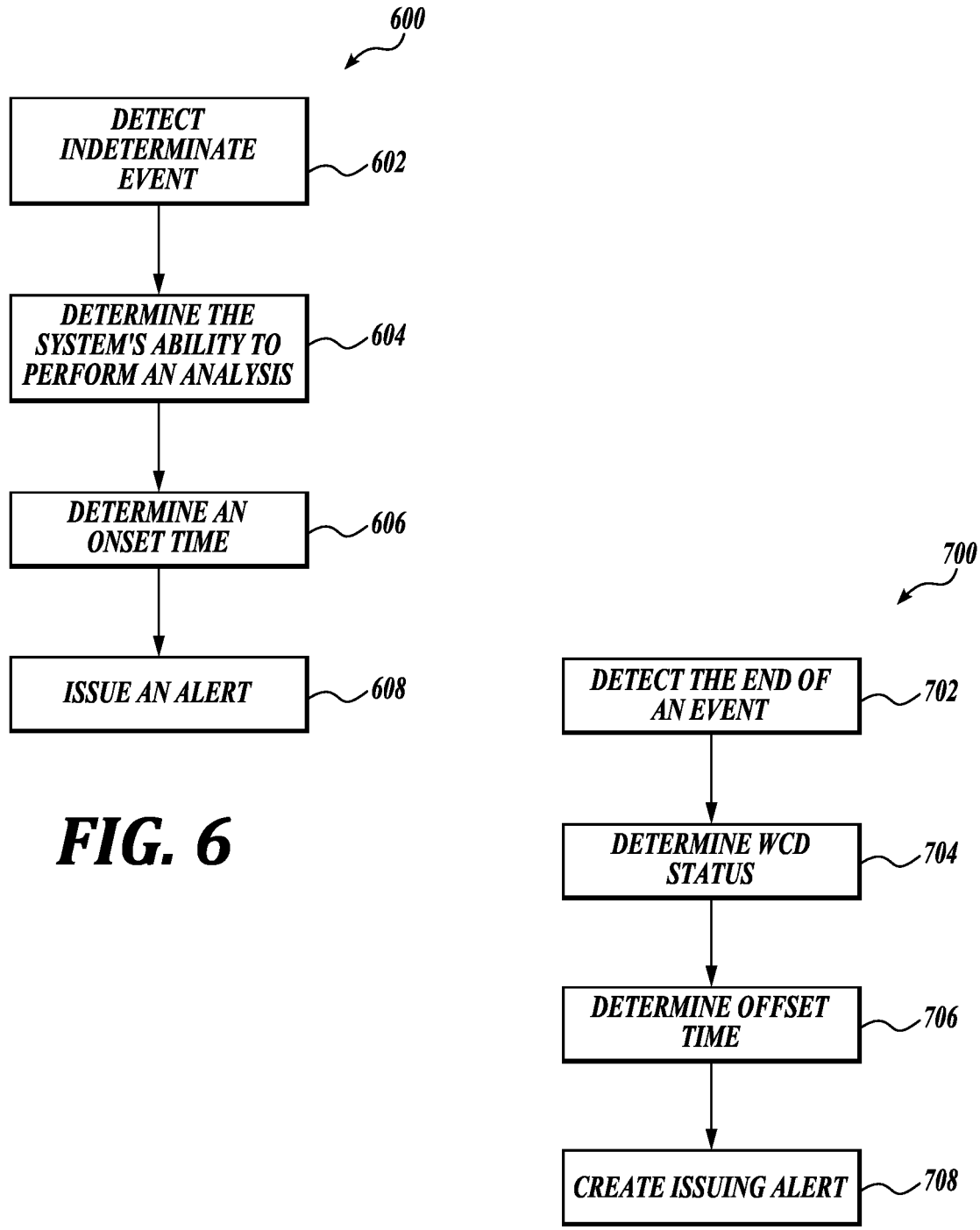

10,957,453 B2

WCD SYSTEM ALERT ISSUANCE AND RESOLUTION

BACKGROUND

Heart arrhythmias may reduce blood flow to various parts of the body. In some instances, arrhythmias result in a Sudden Cardiac Arrest (SCA) where a person's heart suddenly and unexpectedly stops beating. If this occurs, blood may stop flowing to the brain and other vital organs. SCA can lead to death very quickly, sometimes within minutes, unless action is quickly taken.

Some people have an increased risk of SCA. This includes people who have had a heart attack, a prior SCA episode, among other risk factors. Frequently, these people are recommended for an Implantable Cardioverter Defibrillator ("ICD"). The ICD is a small electronic device connected to the heart that continuously monitors the person's electrocardiogram ("ECG"). If or when the ICD detects certain types of heart arrhythmias or abnormalities, the ICD delivers an electric pulse or shock to the patient's heart.

A patient may have a period of time between being recommended for an ICD and receiving one. In the interim timeframe, a patient may be suited with a Wearable Cardioverter Defibrillator ("WCD") system. A WCD system is worn by the patient and includes, among other components, a defibrillator and one or more external electrodes. When a patient wears a WCD system, the WCD may monitor several patient parameters, including the patient's ECG. If a potentially life-threatening arrhythmia is detected, then the defibrillator may be activated and primed to deliver an appropriate electric shock through the patient's body which also shocks the heart.

When a patient is given a WCD, the patient typically must interact with the system to ensure the system is functioning properly, to receive input and stats from the WCD, and to provide feedback when needed. The WCD may provide alerts or status indicators to the patient.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one embodiment, a WCD is described. The WCD includes a support structure configured to be worn by a patient and a processor coupled to the support structure. The WCD also includes an energy storage module configured to store an electrical charge and in communication with the processor. The WCD also includes a discharge circuit coupled to the energy storage module, the discharge circuit in communication with the processor and configured to discharge the stored electrical charge through a body of the patient. The processor is configured to detect an event at the WCD, classify the detected event, and determine an alarm onset time of the detected event based at least in part on the event classification. The processor is further configured to issue the alarm after the alarm onset time.

In some embodiments, the processor is further configured to determine if the detected event has ended. The processor may also determine an offset time for ceasing the issued alarm based at least in part on the end of the event and the event classification. In some embodiments, detecting the event at the WCD may include detecting the event using one of an algorithm detection, performance issue, or a combination thereof. In an embodiment, classifying the event may include determining if the event is one of a health condition, binary event, or an indeterminate event. In some embodiments, a binary event may be a discernable event with a singular determine factor. In further embodiments, an indeterminate event requires analysis to determine if the condition exists. In an embodiment, the processor is configured to determine a severity of the detected event. In some embodiments, the onset time is based at least in part on the determined severity of the event. In an embodiment, the processor may be further configured to detect an indeterminate event using algorithm detection of performance issues. In a further embodiment, the onset time may be based at least in part on physical equipment sensing for alert conditions associated with physical equipment issues. In another embodiment, the onset time may be based at least in part on electrical equipment sensing for alert conditions associated with electrical equipment issues.

In another embodiment, a method for determining an onset time for an alarm for a WCD system is described. The method includes detecting an event at the WCD. The method also includes classifying the detected event. The method further includes determining an alarm onset time of the detected event based at least in part on the event classification. The method also includes issuing the alarm after the alarm onset time.

In another embodiment, a WCD is described. The WCD includes a support structure configured to be worn by a patient and a processor coupled to the support structure. The WCD also includes an energy storage module configured to store an electrical charge and in communication with the processor. The WCD also includes a discharge circuit coupled to the energy storage module, the discharge circuit in communication with the processor and configured to discharge the stored electrical charge through a body of the patient. The processor is configured to detect an event using one of an algorithm detection, performance issue, or a combination thereof. The processor is also configured to classify the detected event as one of a health condition, binary event, or an indeterminate event and determine an alarm onset time of the detected event based at least in part on the event classification. The processor is configured to issue the alarm after the alarm onset time, determine if the detected event has ended, and determine an offset time for ceasing the issued alarm based at least in part the end of the event and the event classification.

DESCRIPTION OF THE DRAWINGS

FIG. 4 is a flow diagram illustrating an example of a method for providing notifications to the user in accordance with the present disclosure.

FIG. 5 is a flow diagram illustrating another example of a method for providing notifications to the user in accordance with the present disclosure.

FIG. 6 is a flow diagram illustrating another example of a method for providing notifications to the user in accordance with the present disclosure.

FIG. 7 is a flow diagram illustrating another example of a method for providing notifications to the user in accordance with the present disclosure.

DETAILED DESCRIPTION

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed.

In the following description, specific details are set forth to provide a thorough understanding of exemplary embodiments of the present disclosure. It will be apparent to one skilled in the art, however, that the embodiments disclosed herein may be practiced without embodying all the specific details. In some instances, well-known process steps have not been described in detail in order not to unnecessarily obscure various aspects of the present disclosure. Further, it will be appreciated that embodiments of the present disclosure may employ any combination of features described herein.

Wearable Cardioverter Defibrillators (WCD) are worn by patients at risk for sudden cardiac arrest. When a patient wears a WCD, the WCD may issue alerts to inform the user of system detected events that require patient action or alert users/bystanders of detected physiological events. The alerts may relate to a device status, equipment, and physiologic alerts. The alerts may become bothersome, irksome, and/or ubiquitous resulting in patient annoyance. If a patient becomes frequently bothered by the WCD, the patient may cease to wear the WCD.

To reduce patient irritation and increase patient compliance, the WCD may implement a user interface design which may include delaying the issuance and resolution of alerts to allow the WCD system to confirm the existence or resolution of a condition prior to alerting the patient or ceasing the alert condition, respectively. This delay in the onset or offset of alerts may filter transient conditions and provide patient confidence that an issued alert requires attention. Likewise, the patient may gain confidence that an alert condition has been resolved.

Figure 1:
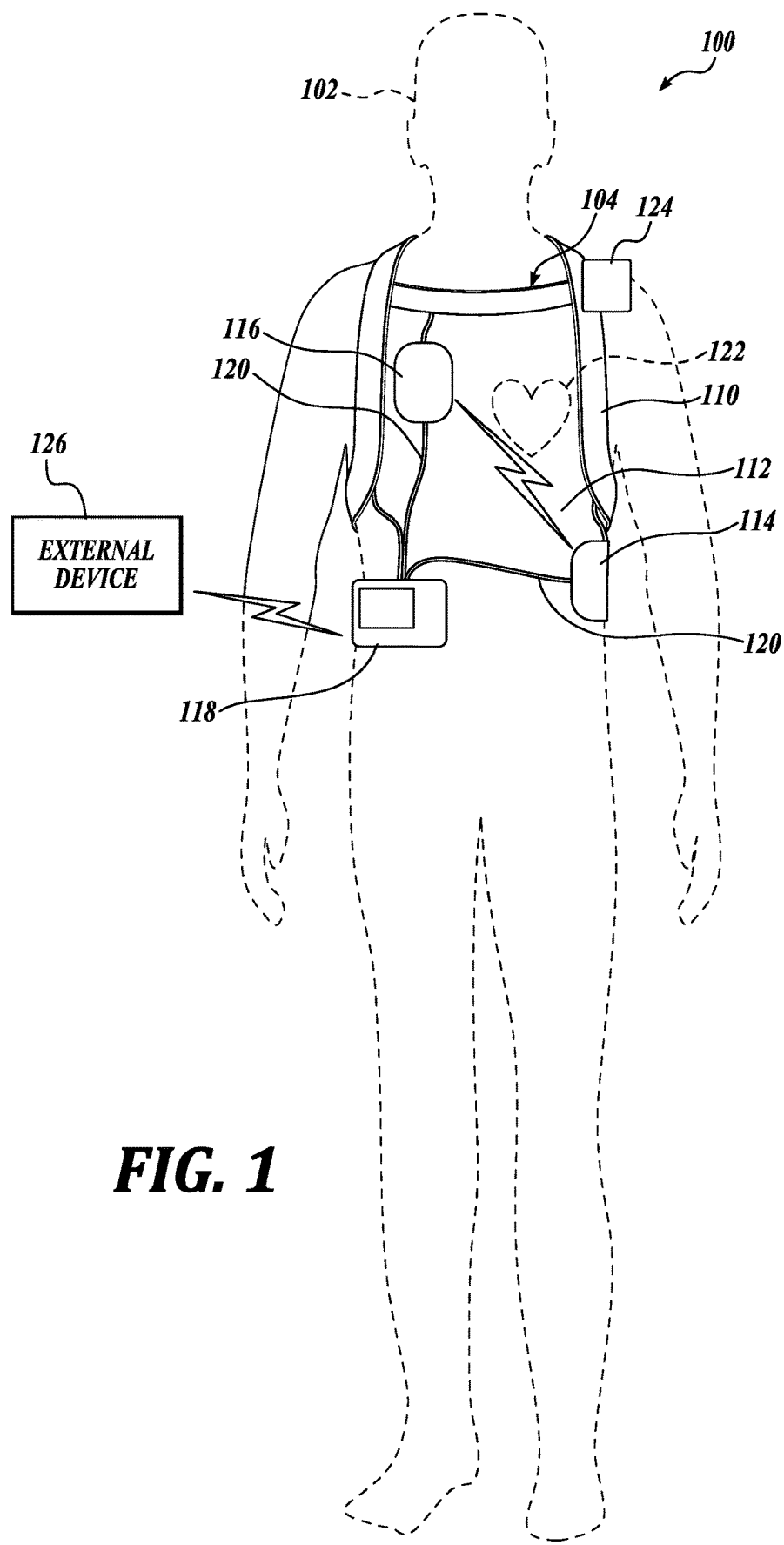
FIG. 1 is a diagram of a sample WCD system in accordance with the present disclosure.

FIG. 1 illustrates a system 100 with a patient 102 wearing an example of a WCD system 104 according to embodiments described herein. The WCD system 104 may include a support structure 110, an external defibrillator 118 connected to defibrillation electrodes 114, 116, among other components.

The support structure 110 may be worn by the patient 102. The support structure 110 may include a vest, shirt, series of straps, or other system enabling the patient 102 to carry at least a portion of the WCD system 104 on the patient's body. In some embodiments, the support structure 110 may comprise a single component. For example, the support structure 110 may comprise a vest or shirt that properly locates the WCD system 104 on a torso 112 of the patient 102. The single component support structure 110 may additionally carry or couple to the various components of the WCD system 104.

In other embodiments, the support structure 110 may comprise multiple components. For example, the support structure 110 may include a first component resting on a patient's shoulders. The first component may locate a series of defibrillation electrodes 114, 116 on the torso 112 of the patient 102. A second component may rest more towards the patient's hips, whereby the second component may be positioned such that the patient's hips support the heavier components of the WCD system 104. In some embodiments, the heavier components of the WCD system 104 may be carried via a shoulder strap or may be kept close to the patient 102 such as in a cart, bag, stroller, wheel chair, or other vehicle.

The external defibrillator 118 may be coupled to the support structure 110 or may be carried remotely from the patient 102. The external defibrillator 118 may be triggered to deliver an electric shock to the patient 102 when patient 102 wears WCD system 104. For example, if certain thresholds are exceeded or met, the external defibrillator 118 may engage and deliver a shock to the patient 102.

The WCD system 104 may defibrillate the patient 102 by delivering an electrical charge to the patient 102 through a series of electrodes 114, 116 positioned on the torso 112. The electrodes 114, 116 may be electrically coupled to the external defibrillator 118 via a series of electrode leads 120. The defibrillator 118 may administer an electric shock to the body of the patient 102 when the defibrillation electrodes 114, 116 are in good electrical contact with the torso 112 of patient 102. In some embodiments, devices (not shown) proximate the electrodes 114, 116 may emit a conductive fluid to encourage electrical contact between the patient 102 and the electrodes 114, 116. The electric shock may be a defibrillation shock, which may go through a heart 122 of the patient 102 in an attempt to restart the heart 122. The brief, strong electric pulse may work to restart the heart 122 which may save the patient's life.

In some embodiments, the WCD system 104 may also include either an external or internal monitoring device or some combination thereof. FIG. 1 displays an external monitoring device 124 which may also be known as an outside monitoring device. The monitoring device 124 may monitor at least one local parameter. Local parameters may include physical state of the patient 102 such as ECG, movement, heartrate, pulse, temperature, and the like. Local parameters may also include a parameter of the WCD 104, environmental parameters, or the like. The monitoring device 124 may be physically coupled to the support structure 110 or may be proximate the support structure 110. In either location, the monitoring device 124 is communicatively coupled with other components of the WCD 104.

In some embodiments, the defibrillator 118 may connect with one or more external devices 126. For example, as shown in FIG. 1, the defibrillator 118 may connect to various external devices 126 such as a cloud computing network, a remote desktop, a laptop, a mobile device, or other external device using a network such as the Internet, local area networks, wide area networks, virtual private networks (VPN), other communication networks or channels, or any combination thereof. In some embodiments, defibrillator may include a screen and one or more user inputs to enable the patient to interact with the WCD system 104. In some embodiments, the patient 102 may view patient data, dismiss a shock if the patient 102 is still conscious, turn off an alarm, and otherwise engage with the WCD system 104 via the defibrillator 118.

Figure 2:
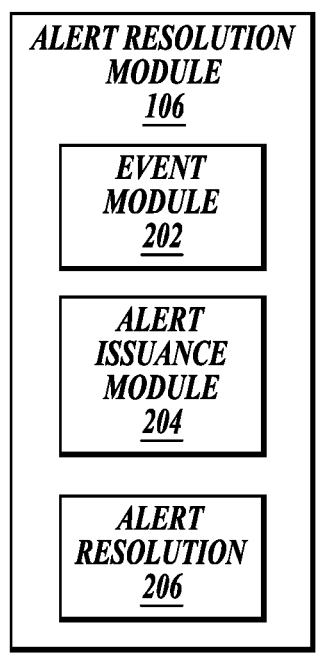
FIG. 2 is a diagram of an example notification module in accordance with the present disclosure.

FIG. 2 is a block diagram illustrating one example of a notification module 106. The notification module 106 may be communicatively coupled to the defibrillator 118. In this example, the notification module 106 has an event module 202, an alert issuance module 204, and an alert resolution module 206.

The event module 202 may detect a system condition which may require an alert. The event module 202 may then determine a type of event, either binary or indeterminate, and then determine a severity of the event. In some instances, the event module 202 may use a combination of sources to determine the overall alert behavior including the type of alert issued, the severity of the alert, the timing of the alert, a length of the alert, and the like. For example, the event module 202 may use an algorithm determination, physical equipment sensing, electrical equipment sensing, or a combination thereof. The algorithm determination may be used for event conditions associated with algorithm detection, performance issues, or a combination thereof. Physical and electrical equipment sensing may be used for event conditions associated with either physical or electrical equipment issues.

In some embodiments, a binary event may be a distinct event with a singular determinating factor that can be ascertained without a quantitative analysis. The binary condition either exists or it does not. For example, an ECG lead or ECG electrode may be disconnected from the defibrillator, a battery may have a low charge or full charge, a defibrillator electrode may be disconnected, and the like. Generally stated, binary conditions are conditions with discernable conditions with singular determination.

An indeterminate event may include an event that requires a process or algorithm to determine if the event exists. For example, in some instances, an ECG electrode may become disconnected or not optimally attached to the patient's skin, a signal being transmitted to the defibrillator may include extra noise, or some other issue may be present with receiving an accurate and clear reading from a component of the WCD.

The event module 202 may determine if there is a potential event and the severity of the event. For example, in some embodiments, while an event may have occurred, the event may not alter or inhibit the ability of the WCD system to function. For example, if a single ECG electrode is misconnected, the event may require resolution but not necessarily immediate resolution. However, if more than one ECG electrode has become disconnected, this may necessitate prompt attention because the WCD may be unable to properly ascertain the patient's health from the remaining electrode readings. Therefore, in some embodiments, some events may require more immediate rectification.

The event module 202 may determine which WCD conditions require resolution to ensure safety and efficacy of a WCD. However, some of these alerts may cause patient frustration due to over-alerting. For example, ECG electrode sensing issues including insufficient ECG contact (analysis not possible), ECG electrodes off (analysis possible); excessive noise and defibrillator pads off may require remediation but also result in over alerting the patient.

In some embodiments, to reduce excessive alerting, the event module 202 may detect system information using algorithm determination associated with the algorithm detection or performance issues. In another embodiment, the event module 202 detects system information from physical equipment sensing, electrical equipment sensing, or both. In some embodiments, a combination of sources may be used to determine the status of an event and relay the information to the alert issuance module 204, the alert resolution module 206, or both.

Once an event has been detected and categorized, the alert issuance module 204 may determine when to issue an alert, if an alert is issued, type of alert, and an urgency of the alert, among other things. For example, each event type may use a different alert onset time. In some embodiments, binary conditions may have shorter onset times than indeterminate conditions. For example, the WCD system may perform startup check when the system is booting. The onset time for startup equipment statuses may be negligible to provide immediate user feedback. A negligible onset time may enable the patient to immediately address any inaccuracies or errors in the system.

In some embodiments, assembly equipment status may be slightly delayed as the system is being assembled. A delay may enable the system to confirm the equipment is properly connected and functioning prior to alerting the patient. For example, assembly equipment status may be delayed by about 1-10 seconds.

In some embodiments, binary equipment statuses during operation may have a varying length of alert issuance delay. For example, equipment status may include if the user needs to press an alert button, if service is required, if service is needed, if the battery is critically low, if the user received treatment, and the like. These types of statuses may delay alert issuance by approximately 1-10 seconds.

Indeterminate conditions may have different onset times. For example, indeterminate conditions may include poor or not connected defibrillator pad contact, ECG electrode or wire contact issues, or the like. The alert issuance module 204 may vary the onset time of an alert. For example, some conditions may not need immediate remediation, such as a single ECG electrode being either detached, not attached properly, or otherwise experiencing noise from one or more leads. In this example, the system may continue to operate properly, although perhaps not optimally, and therefore, immediate attention is not required but prompt attention is desired. Therefore, the alert issuance module 204 may have an onset alert of 10 to 30 minutes. In some embodiments, the alert onset time may be about 15 minutes. In further embodiments, the onset time may be between about 5 and about 10 minutes.

In another embodiment, the condition may necessitate prompt resolution. For example, if multiple ECG electrodes are improperly situated or misconnected, the WCD system may not be able to properly analyze the patient's health conditions or function properly or safely. For example, the WCD system may be unable to accurately determine a health status of the patient. Likewise, if a defibrillator pad is incorrectly adhered to the skin of the patient or is experiencing noise, faulty connections, or other potential issues, the WCD may be unable to deliver a necessary shock to revive a patient if a health event occurs. If a health risk is present, the alert issuance module 204 may have an alert onset time of about 10 to about 20 minutes. This predetermined time frame may vary with the severity of the event and the potential for the WCD system to properly function and treat the patient.

In another embodiment, if a physiologic condition has been confirmed, the alert issuance module 204 may have a zero-onset time. For example, if the WCD system detects a cardiac event or another health event, the alert may immediately issue to alert the patient to a potentially life-threatening condition.

This alert scheme allows the WCD to provide user feedback quickly for distinct conditions while delaying user feedback for conditions that may resolve on their own without user action needed.

The alert resolution module 206 may use an "offset time" to delay the cessation of alerts. This offset time may have different durations or for different predetermined time periods based at least in part on the underlying event, the type of alarm, the duration of the initial alarm, received patient feedback, and the like.

In some embodiments, an alert about a detected system condition with distinct binary results, such as discussed previously, may have a shorter offset time. For example, when the WCD system is booting, there may be a zero-offset time for startup equipment statuses. For confirmed physiologic detections, like when the WCD system is no longer detecting an irregular heartbeat, the offset time may be negligible. A short offset time, between about 1 and about 10 seconds, may be utilized for assembly equipment status such as the WCD being assembled. This short duration time, such as between about 1 and about 10 seconds, may also be utilized for equipment statuses during WCD operation.

The alert resolution module 206 may have a longer offset time for system conditions with indeterminate results. In some embodiments, such as excessive noise in an ECG electrode or lead, or a defibrillator electrode or lead affecting the ability of the WCD system to perform analysis, the alert resolution module 206 may have an offset time between about 1 and about 10 seconds. Other events, such as disconnected defibrillator pads, may have longer offset times between 1 second and 60 seconds. The offset time may allow the alert resolution module 206 to provide user feedback quickly for distinct resolved conditions while delaying user feedback for conditions that may not actually be fixed and require additional user action to resolve.

Figure 3:
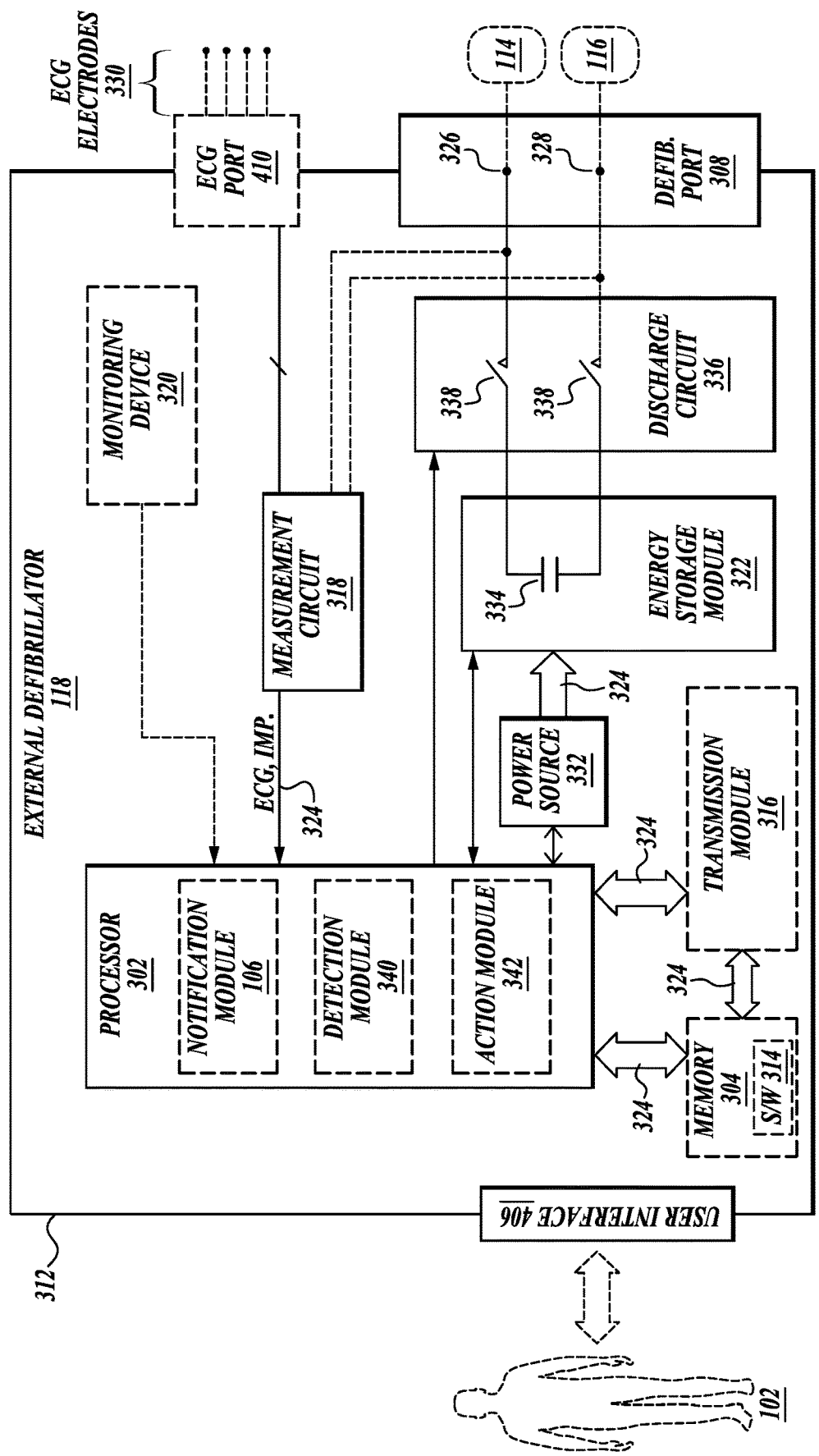
FIG. 3 is a block diagram of an example of a defibrillator unit of the environment shown in FIG. 1 in accordance with one example of the present disclosure.

FIG. 3 is a diagram displaying various functional components of one example of a defibrillator 118. The defibrillator 118 may be an example of the defibrillator 118 described with reference to FIG. 1. The components shown in FIG. 3 may be contained within a single unit or may be separated amongst two or more units in communication with each other. The defibrillator 118 may include a processor 302, memory 304, user interface 306, defibrillation port 308, ECG port 310, among other components. In some embodiments, the components are contained within a housing 312 or casing. The housing 312 may comprise a hard shell around the components or may comprise a softer shell for increased patient comfort.

The processor 302, memory 304 (including software/firmware code (SW) 314), user interface 306, defibrillation port 308, ECG port 310, transmission module 316, measurement circuit 318, monitoring device 320, and energy storage module 322 may communicate—directly or indirectly—with one another (e.g., via one or more buses 324). One or more buses 324 may allow data communication between one or more elements and/or modules of the defibrillator 118.

The memory 304 may include random access memory (RAM), read only memory (ROM), flash RAM, and/or other types. The memory 304 may store computer-readable, computer-executable software/firmware code 314 including instructions that, when executed, cause the processor 302 to perform various functions (e.g., determine shock criteria, determine consciousness of patient, track patient parameters, etc.). In some embodiments, the processor 302 may include an intelligent hardware device, e.g., a central processing unit (CPU), a microcontroller, an application-specific integrated circuit (ASIC), etc.

In some embodiments, the memory 304 can contain, among other things, the Basic Input-Output system (BIOS) which may control basic hardware and/or software operations such interactions and workings of the various components of the defibrillator 118, and in some embodiments, components external to the defibrillator 118. For example, the memory 304 may contain various modules to implement the workings of the defibrillator 118 and other aspects of the present disclosure.

In some embodiments, the defibrillator 118 may include a user interface 306. The user interface 306 may enable the patient to view one or metrics concerning the defibrillator 118, the WCD system as a whole, or some combination thereof. For example, the user interface 306 may display an ECG of the patient, a status of the defibrillator 118, a status of a charge (e.g. a battery charge or an energy storage module), and the like.

In some embodiments, the defibrillator 118 may include a defibrillation port 308. The defibrillation port 308 may comprise a socket, opening, or electrical connection in the housing 312. In some instances, the defibrillation port 308 may include two or more nodes 326, 328. The two or more nodes 326, 328 may accept two or more defibrillation electrodes (e.g. defibrillation electrodes 114, 116, FIG. 1). The nodes 326, 328 may provide an electrical connection between the defibrillation electrodes 114, 116 and the defibrillator 118. The defibrillation electrodes 114, 116 may plug into the two or more nodes 326, 328 via one or more leads (e.g. leads 120), or, in some instances, the defibrillation electrodes 114, 116 may be hardwired to the nodes 326, 328. Once an electrical connection is established between the defibrillation port 308 and the electrodes 114, 116, the defibrillator 118 may be able to deliver an electric shock to the patient.

In some embodiments, the defibrillator 118 may include an ECG port 310 in the housing 312. The ECG port 310 may accept one or more ECG electrodes 330 or ECG leads. In some instances, the ECG electrodes 330 sense a patient's ECG signal. For example, the ECG electrodes 330 may record electrical activity generated by the heart muscle depolarization. The ECG electrodes 330 may utilize 3-leads to 12-leads or multichannel ECG, or the like. The ECG electrodes 330 may connect with the patient's skin.

In some embodiments, the defibrillator 118 may include a measurement circuit 318. The measurement circuit 318 may be in communication with the ECG port 310. For example, the measurement circuit 318 may receive physiological signals from ECG port 310. The measurement circuit 318 may additionally or alternatively receive physiological signals via the defibrillation port 308 when defibrillation electrodes 114, 116 are attached to the patient. The measurement circuit 318 may determine a patient's ECG signal from a difference in voltage between the defibrillation electrodes 114, 116.

In some embodiments, the measurement circuit 318 may monitor the electrical connection between the defibrillation electrodes 114, 116 and the skin of the patient. For example, the measurement circuit 318 can detect impedance between the electrodes 114, 116. In some embodiments, the detected impedance may indicate the effective resistance of an electric circuit. An impedance calculation may, at least in part, determine when the electrodes 114, 116 have a good electrical connection with the patient's body.

In some embodiments, the defibrillator 118 may include an internal monitoring device 320 within the housing 312. The monitoring device 320 may monitor at least one local parameter. Local parameters may include physical state of the patient such as ECG, movement, heartrate, pulse, temperature, and the like. Local parameters may also include a parameter of the WCD (e.g. WCD 104), defibrillator 118, environmental parameters, or the like.

In some embodiments, a WCD (e.g. WCD 104) may include an internal monitoring device 320 and an external monitoring device (e.g. external monitoring device 124). If both monitoring devices 124, 320 are present, the devices 124, 320 may collaborate to parse out specific parameters depending on position, location, and other factors. For example, the external monitoring device 124 may monitor environmental parameters while the internal monitoring device 320 may monitor patient and system parameters.

In some embodiments, the defibrillator 118 may include a power source 332. The power source 332 may comprise a battery or battery pack, which may be rechargeable. In some instances, the power source 332 may comprise a series of different batteries to ensure the defibrillator 118 has power. For example, the power source 332 may include a series of rechargeable batteries as a prime power source and a series of non-rechargeable batteries as a secondary source. If the patient is proximate an AC power source, such as when sitting down, sleeping, or the like, the power source 332 may include an AC override wherein the power source 332 draws power from the AC source.

In some embodiments, the defibrillator 118 may include an energy storage module 322. The energy storage module 322 may store electrical energy in preparation or anticipation of providing a sudden discharge of electrical energy to the patient. In some embodiments, the energy storage module 322 may have its own power source and/or battery pack. In other embodiments, the energy storage module 322 may pull power from the power source 332. In still further embodiments, the energy storage module 322 may include one or more capacitors 334. The one or more capacitors 334 may store an electrical charge, which may be administered to the patient. The processor 302 may be communicatively coupled to the energy storage module 322 to trigger the amount and timing of electrical energy to provide to the defibrillation port 308 and, subsequently, the patient.

In some embodiments, the defibrillator 118 may include a discharge circuit 336. The discharge circuit 336 may control the energy stored in the energy storage module 322. For example, the discharge circuit 336 may either electrical couple or decouple the energy storage module 322 to the defibrillation port 308. The discharge circuit 336 may be communicatively coupled to the processor 302 to control when the energy storage module 322 and the defibrillation port 308 should or should not be coupled to either administer or prevent a charge from emitting from the defibrillator 118. In some embodiments, the discharge circuit 336 may include one or more switches 338. The one or more switches 338 may include an H-bridge.

In some embodiments, the defibrillator 118 may include a transmission module 316. The transmission module 316 may establish one or more communication links with either local hardware and/or software to the WCD and defibrillator 118 or to remote hardwire separate from the WCD system. In some embodiments, the transmission module 316 may include one or more antennas, processors, and the like. The transmission module 316 may communicate wirelessly via radio frequency, electromagnetics, local area networks (LAN), wide area networks (WAN), virtual private networks (VPN), RFID, Bluetooth, cellular networks, and the like. The transmission module 316 may facilitate communication of data and commands such as patient data, episode information, therapy attempted, CPR performance, system data, environmental data, and so on.

In some embodiments, the processor 302 may execute one or more modules. For example, the processor 302 may execute a detection module 340 and/or an action module 342. The detection module 340 may be a logic device or algorithm to determine if any thresholds are exceeded which may require action of the defibrillator 118. For example, the detection module 340 may receive and interpret all the signals from the ECG port 310, the defibrillation port 308, the monitoring device 320, an external monitoring device, and the like. The detection module 340 may process the information to ensure the patient is conscious and healthy. If any parameter indicates the patient may be experiencing distress or indicating a cardiac episode, the detection module 340 may activate the action module 342.

The action module 342 may receive data from the detection module 340 and perform a series of actions. For example, an episode may merely be a loss of batter power at the power source 332 or the energy storage module 322, or one or more electrodes (e.g., ECG electrodes, defibrillation electrodes) may have lost connection. In such instances, the action module 342 may trigger an alert to the patient or to an outside source of the present situation. If an episode is a health risk, such as a cardiac event, the action module 342 may begin a series of steps. This may include issuing a warning to the patient, issuing a warning to a third party, priming the energy storage module 322 for defibrillation, releasing one or more conductive fluids proximate defibrillation electrodes 114, 116, and the like.

In further embodiments, the processor 302 may also execute the notification module 106. The notification module 106 may detect the working functions of the WCD system, categorize the type of event, and determine what alert to issue to the patient and when the alert is issued. The notification module 106 may also determine or receive data to determine when an event has been resolved. Event resolution may cause the notification module 106 to cease an alert, issue a resolution notice, or a combination thereof.

FIG. 4 is a flow chart illustrating an example of a method 400 for WCD systems, in accordance with various aspects of the present disclosure. For clarity, the method 400 is described below with reference to aspects of one or more of the systems described herein. In some examples, a defibrillator (e.g. defibrillator 118) may perform one or more of the functions described below. In other embodiments, a communication device coupled to the defibrillator or the WCD system may perform one or more of the functions described below.

At block 402, the method 400 may include detecting an event at the WCD system. The event may be a system event, such as an error with the actual system and hardware or it may be a health event such as poor readings from a sensor, poor connectivity, an abnormal ECG, or the like.

At block 404, the method 400 may include classifying the event. If a safety or health concern is detected, the method 400 may revert to emergency procedures such as shocking the patient. In further embodiments, the method 400 may also determine if the event is a binary event or an indeterminate event. A binary event may be a status of equipment with a distinct and finite determination such as a disconnected plug, a status of the battery, and the like. An indeterminate event may include defibrillator pad contact or lack thereof, ECG electrode contact issues or noise from a reading of one or more ECG electrodes or leads, and the like. An algorithm may determine the feed from one of these sources is faulty providing a lack of ability to perform an analysis or may include noise or other errors such that, while the WCD system may still be able to analyze the data sufficiently, the event still requires correction.

At block 406, the method 400 may include determining an onset time of the alert or an offset time of the alert (if the event has been resolved). The onset time and offset time may depend, at least in part, on the type of detected event. For example, for confirmed physiologic conditions, the onset time may be negligible. This may include a cardiac event, an abnormal ECG, or other health concern.

In further embodiments, if a patient or user is starting up or booting the WCD system, the method 400 may have a small to negligible onset time for startup equipment statuses. This may enable a patient to immediately ascertain an issue or other condition with the equipment that can be quickly remedied prior the patient wearing the system. Similarly, if the WCD system is being assembled, the method 400 may slightly delay the onset of an alert to enable the patient to properly assemble the system. For example, the onset time may be between about 1 and about 10 seconds prior to alerting the patient.

If the WCD system is active and in use, the method 400 may delay the onset of alerts for binary equipment statuses. For example, the alert may include if the patient needs to press an alert button, if service is required, if the battery is critically low, if a lead or other connector became unplugged, and the like. The method 400 may delay the onset of the alert between about 1 and about 5 seconds. Further conditions may have alerts delayed different times, such as between 0 and about 60 seconds.

If the event is an indeterminate event, the method 400 may have a longer onset time prior to issuing an alert. For example, the onset time may vary between about 1 minute and about 15 minutes, or in some embodiments, as long as 20 to even 30 minutes. In some embodiments, the ability of the system to perform an analysis may correlate to a length of onset time. For example, if there is an ECG contact or excessive noise issues that affect the ability of the system to perform an analysis, the method 400 may have a shorter onset time between about 1 and about 5 minutes. If the ECG has contact issues which do not affect the ability of the system to perform an analysis, the method 400 may have a longer onset time of between about 15 and about 30 minutes. In further embodiments, if the event detected is a contact issue with defibrillator pads, the system may determine a length of time the event is present. If the event or condition has been present for a predetermined length of time, in some embodiments between about 10 and about 20 minutes, the method 400 may then have an onset time of between about 10 and about 20 minutes.

In some embodiments, the offset time to delay the cessation of alerts may closely follow the onset time. The offset time may be predetermined based at least in part on the alert condition. For example, for binary events such as startup equipment status, assembly equipment status, or equipment status during operation, the offset may be between about 0 seconds and about 10 seconds. If a confirmed physiologic condition is no longer being detected, the offset time may be negligible.

Further, in some embodiments, if the event is an indeterminate event, the method 400 may delay the cessation of an alert by a different predetermined time period. For example, if excessive noise issues, which may affect the ability to perform an analysis, the offset time may be between about 5 and about 15 seconds.

At block 408, the method 400 may include issuing the alert after the predetermined onset has passed. The method 400 may also include ceasing the alert after a predetermined offset time period has passed.

Thus, the method 400 may provide for issuing alerts after a predetermine onset time based at least in part on the type of event detected. It should be noted that the method 400 is just one implementation and that the operations of the method 400 may be rearranged or otherwise modified such that other implementations are possible.

FIG. 5 is a flow chart illustrating an example of a method 500 for WCD systems, in accordance with various aspects of the present disclosure. For clarity, the method 500 is described below with reference to aspects of one or more of the systems described herein. In some examples, a defibrillator (e.g. defibrillator 118) may perform one or more of the functions described below. In other embodiments, a communication device coupled to the defibrillator or the WCD system may perform one or more of the functions described below.

At block 502, the method 500 may include detecting a binary event. The binary event may include startup equipment statuses, confirmed physiological conditions, assembly equipment statuses, equipment statuses during operation, and the like. When a binary event is detected, the method 500 proceeds to block 504.

At block 504, the method 500 may include determining a status of the WCD system. The status may include an operational status, such as whether the WCD is being assembled, booting, being disassembled, or in operation.

At block 506, the method 500 may include determining an onset time. The onset time may be based in part on the type of binary event and the status of the WCD system during the time period the binary event was detected. For example, if the WCD system is being assembled, the onset time may be between about 1 and about 10 seconds for equipment statuses. If the WCD system is booting, the onset time may be negligible for startup equipment statuses. If the WCD system is operational, the onset time may be between 1 and 10 seconds for operational equipment statuses. If the WCD system is operational and fully functioning and a cardiac event is detected, the onset time may be negligible. Once an onset time is determined, at block 508, the method 500 may include issuing an alert after the predetermined onset time.

Thus, the method 500 may provide for issuing alerts after a predetermine onset time based at least in part on the type of event detected. It should be noted that the method 500 is just one implementation and that the operations of the method 500 may be rearranged or otherwise modified such that other implementations are possible.

FIG. 6 is a flow chart illustrating an example of a method 600 for WCD systems, in accordance with various aspects of the present disclosure. For clarity, the method 600 is described below with reference to aspects of one or more of the systems described herein. In some examples, a defibrillator (e.g. defibrillator 118) may perform one or more of the functions described below. In other embodiments, a communication device coupled to the defibrillator or the WCD system may perform one or more of the functions described below.

At block 602, the method 600 may include detecting an indeterminate event. The indeterminate event such an issue with defibrillator pad contact, ECG contact issues, or noise issues, or the like. When an indeterminate event is detected, the method 600 proceeds to block 604.

At block 604, the method 600 may include determining the system's ability to perform an analysis. For example, if one ECG electrode has an issue, the system may still be able to perform sufficient analysis. However, in some embodiments, if more than one ECG electrode has an issue, the system may be unable to perform a sufficient health analysis to determine a health status of the patient. In other instances, a defibrillator pad may be disconnected or misconnected resulting in the in ability for the system to deliver a shock to the patient. In other instances, the detected indeterminate event may have no effect on the ability of the system to perform an analysis.

At block 606, the method 600 may include determining an onset time based at least in part on the detected event and the system's ability to perform an analysis. The predetermined onset time may be between about 1 minute and about 30 minutes. In some embodiments, if the system cannot perform an analysis, such an improperly function ECG electrode, the onset time may be between about 30 seconds and about 5 minutes. In other embodiments, if the system is properly functioning, the onset time may be between about 10 minutes and about 20 minutes. After the predetermined onset time has been determined and passed, at block 608, the method 600 may include issuing an alert.

Thus, the method 600 may provide for issuing alerts after a predetermine onset time based at least in part on the type of event detected. It should be noted that the method 600 is just one implementation and that the operations of the method 600 may be rearranged or otherwise modified such that other implementations are possible.

FIG. 7 is a flow chart illustrating an example of a method 700 for WCD systems, in accordance with various aspects of the present disclosure. For clarity, the method 700 is described below with reference to aspects of one or more of the systems described herein. In some examples, a defibrillator (e.g. defibrillator 118) may perform one or more of the functions described below. In other embodiments, a communication device coupled to the defibrillator or the WCD system may perform one or more of the functions described below.

At block 702, the method 700 may include detecting the end of an event. The event may be a binary event or an indeterminate event. The end of the event may be detected through equipment sensing or through an algorithm. For example, most binary conditions may be detected through equipment sensing. In some embodiments, an end of the indeterminate events may be determined through an algorithm where received information is processed and determined the system is properly functioning.

At block 704, the method 700 may include determining a status of the WCD. If the WCD system is starting up, booting, or being assembled or disassembled. The system may also be in operation and functioning normally. In other embodiments, sensors or other equipment may be in proper communication within the WCD system.

At block 706, the method 700 may include determining an offset time based at least in part on the initial event, the end of the event, and the status of the WCD system. For example, if the system is booting and an event was detected and ceased, the method 700 may have a negligible offset for ceasing the alarm. Similarly, if the system is being assembled, an offset time may be negligible. If confirmed physiological statuses are no longer being detected, the method 700 may have a negligible offset time. If an equipment status during operation is no longer detected, the method 700 may have about 1 to 5 seconds of offset time. If excessive noise issues from various signals are no longer detected, the method 700 may have an offset time of about 10 to about 15 seconds. In some embodiments, offset times may be longer, such as about 60 seconds to about 5 minutes, to fully determine the event has ceased. Once an offset time has been determined, at block 708, the method 700 may include ceasing the issued alert.

Thus, the method 700 may provide for ceasing issued alerts after a predetermine onset time based at least in part on the type of event detected. It should be noted that the method 700 is just one implementation and that the operations of the method 700 may be rearranged or otherwise modified such that other implementations are possible.

This document may include references to directions, such as "forward," "rearward," "front," "rear," "upward," "downward," "top," "bottom," "right hand," "left hand," "lateral," "medial," "in," "out," "extended," etc. These references, and other similar references, are only to assist in helping describe and to understand the particular embodiments and are not intended to limit the present disclosure to these directions or locations.

The present document may also reference quantities and numbers. Unless specifically stated, such quantities and numbers are not to be considered restrictive, but exemplary of the possible quantities or numbers associated with the present application. Also, in this regard, the present application may use the term "plurality" to reference a quantity or number. The terms "about," "approximately," "near," etc., mean plus or minus 5% of the stated value. For the purposes of the present disclosure, the phrase "at least one of A, B, and C," for example, means (A), (B), (C), (A and B), (A and C), (B and C), or (A, B, and C), including all further possible permutations when greater than three elements are listed.

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

While illustrative embodiments have been illustrated and described, it will be appreciated that various changes can be made therein without departing from the spirit and scope of the disclosure.

We claim:

1. A wearable cardioverter defibrillator (WCD), comprising:
   a support structure configured to be worn by a patient;
   a processor coupled to the support structure;
   an energy storage module configured to store an electrical charge and in communication with the processor;
   a discharge circuit coupled to the energy storage module, the discharge circuit in communication with the processor and configured to discharge the stored electrical charge through a body of the patient; and
   the processor configured to:
      detect an event at the WCD,
      determine if the detected event is not categorized as a life-threatening condition due to lack of a health risk to the patient,
      determine a category of the detected event,
      determine an alarm onset time of the categorized event based on the event category,
      issue the alarm after the alarm onset time,
      determine an offset time for ceasing the issued alarm based on the event category, and
      cease the issued alarm.

2. The WCD of claim 1, wherein the processor is further configured to:
  determine if the detected event has ended, and
  further determine the offset time for ceasing the issued alarm based at least in part on the end of the event.

3. The WCD of claim 1, wherein detecting the event at the WCD further includes:
  detecting the event using one of an algorithm detection, performance issue, or a combination thereof.

4. The WCD of claim 1, wherein classifying categorizing the event includes:
  determining if the event is one of a non-life threatening health condition, binary event, or an indeterminate event.

5. The WCD of claim 4, wherein a binary event is a discernable event with a singular determine factor.

6. The WCD of claim 4, wherein an indeterminate event requires analysis to determine if the event exists.

7. The WCD of claim 1, wherein the processor is further configured to:
  determine a severity of the detected event.

8. The WCD of claim 7, wherein the onset time is based at least in part on the determined severity of the event.

9. The WCD of claim 1, wherein the processor is further configured to:
  detect an indeterminate event using algorithm detection of performance issues.

10. The WCD of claim 1, wherein the onset time is based at least in part on physical equipment sensing for alert conditions associated with physical equipment issues.

11. The WCD of claim 1, wherein the onset time is based at least in part on electrical equipment sensing for alert conditions associated with electrical equipment issues.

12. A method for determining an onset time for an alarm for a wearable cardioverter defibrillator (WCD) system, comprising:
  detecting an event at the WCD,
  determining if the detected event is not categorized as a life-threatening condition due to lack of a health risk to the patient,
  determining a category of the detected event,
  determining an alarm onset time of the categorized event based on the event category,
  issuing the alarm after the alarm onset time,
  determining an offset time for ceasing the issued alarm based on the event category, and ceasing the issued alarm.

13. The method of claim 12, wherein the method further includes:
  determining if the detected event has ended, and
  further determining the offset time for ceasing the issued alarm based the end of the event.

14. The method of claim 12, wherein detecting the event at the WCD further includes:
  detecting the event using one of an algorithm detection, performance issue, or a combination thereof.

15. The method of claim 12, wherein categorizing the event includes:
  determining if the event is one of a non-life threatening health condition, binary event, or an indeterminate event.

16. The method of claim 12, wherein a binary event is a discernable event with a singular determine factor.

17. The method of claim 12, wherein an indeterminate event requires analysis to determine if the event exists.

18. The method of claim 12, further including:
  determining a severity of the detected event.

19. The method of claim 12, further including:
  detecting an indeterminate event using algorithm detection of performance issues.

20. A wearable cardioverter defibrillator (WCD), comprising:
  a support structure configured to be worn by a patient;
  a processor coupled to the support structure;
  an energy storage module configured to store an electrical charge and in communication with the processor;
  a discharge circuit coupled to the energy storage module, the discharge circuit in communication with the processor and configured to discharge the stored electrical charge through a body of the patient; and
  the processor configured to:
    detect an event using one of an algorithm detection, performance issue, or a combination thereof,
    classify the detected event as a binary event that is a discernible event with a singular determine factor,
    determine an alarm onset time of the detected binary event based on the binary event classification,
    issue the alarm after the alarm onset time,
    determine if the detected binary event has ended, and
    determine an offset time for ceasing the issued alarm based at least in part the end of the detected binary event and the binary event classification.

* * * * *

UNITED STATES PATENT AND TRADEMARK OFFICE
CERTIFICATE OF CORRECTION

Page 1 of 1

PATENT NO. : 10,957,453 B2
APPLICATION NO. : 16/542110
DATED : March 23, 2021
INVENTOR(S) : Z. Engman et al.

It is certified that error appears in the above-identified patent and that said Letters Patent is hereby corrected as shown below:

In the Claims

| Column | Line | |
|---|---|---|
| 15 | 10 | "wherein classifying categorizing" to -- wherein categorizing -- |
| 16 | 5 | "based the" to -- based on the -- |
| 16 | 44 | "part the" to -- part on the -- |

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*